US008804117B2

(12) United States Patent
Rigneault et al.

(10) Patent No.: US 8,804,117 B2
(45) Date of Patent: *Aug. 12, 2014

(54) METHOD FOR DETECTING A RESONANT NONLINEAR OPTICAL SIGNAL AND DEVICE FOR IMPLEMENTING SAID METHOD

(75) Inventors: Hervé Rigneault, Allauch (FR); David Gachet, Beaumont-les-Valence (FR); Sophie Brustlein, Marseilles (FR)

(73) Assignee: Centre National de la Recherche Scientifique-CNRS, Paris (FR)

( * ) Notice: Subject to any disclaimer, the term of this patent is extended or adjusted under 35 U.S.C. 154(b) by 6 days.

This patent is subject to a terminal disclaimer.

(21) Appl. No.: 13/574,482

(22) PCT Filed: Jan. 18, 2011

(86) PCT No.: PCT/EP2011/050622
§ 371 (c)(1),
(2), (4) Date: Sep. 12, 2012

(87) PCT Pub. No.: WO2011/089119
PCT Pub. Date: Jul. 28, 2011

(65) Prior Publication Data
US 2013/0021606 A1    Jan. 24, 2013

(30) Foreign Application Priority Data

Jan. 22, 2010  (FR) .................................... 10 00244

(51) Int. Cl.
*G01J 3/44* (2006.01)
(52) U.S. Cl.
USPC .......................................... 356/301; 356/300
(58) Field of Classification Search
USPC ........................... 356/301, 317, 318, 451, 456
See application file for complete search history.

(56) References Cited

U.S. PATENT DOCUMENTS 5,042,952 A    8/1991  Opsal et al.
5,303,710 A *  4/1994  Bashkansky et al. ......... 600/476
(Continued)

FOREIGN PATENT DOCUMENTS

EP   1278092 A2   1/2003
EP   2096430 A2   9/2009
(Continued)

OTHER PUBLICATIONS

International Search Report for International Application No. PCT/EP2011/050622 mailed May 17, 2011 (6 pages).

(Continued)

*Primary Examiner* — Tarifur Chowdhury
*Assistant Examiner* — Michael P Lapage
(74) *Attorney, Agent, or Firm* — Osha Liang LLP

(57) ABSTRACT

A method and device for detecting a resonant non-linear optical signal induced in a sample, the sample including a resonant medium and a non-resonant medium forming an interface. The device includes an emission source of at least one first excitation light beam, called a pump beam, at a given angular frequency $\omega_p$ for the excitation of the resonant medium of said sample, an optical detection module for detecting a non-linear optical signal resulting from the interaction of said pump beam with an axial interface between the resonant and non-resonant media of the sample, in at least two symmetrical directions ($\vec{k}, \vec{k}'$) relative to the optical axis of said excitation beam incident in the sample, and a processing unit for processing signals ($I^{Fwd}(\vec{k}), I^{Fwd}(\vec{k}')$) thus detected, allowing the difference between said signals to be obtained.

28 Claims, 9 Drawing Sheets

(56) References Cited

U.S. PATENT DOCUMENTS

| | | | |
|---|---|---|---|
| 5,493,443 A * | 2/1996 | Simon et al. | 359/368 |
| 6,789,507 B1 | 9/2004 | Slate et al. | |
| 6,809,814 B2 | 10/2004 | Xie et al. | |
| 7,352,458 B2 | 4/2008 | Xie et al. | |
| 2006/0192969 A1* | 8/2006 | Marks et al. | 356/451 |
| 2006/0238745 A1* | 10/2006 | Hashimoto et al. | 356/73 |
| 2007/0091305 A1 | 4/2007 | Xie et al. | |

FOREIGN PATENT DOCUMENTS

| | | |
|---|---|---|
| WO | 2005/124322 A1 | 12/2005 |
| WO | 2008135257 A1 | 11/2008 |

OTHER PUBLICATIONS

D. Gachet et al., "Coherent anti-Stokes Raman scattering (CARS) microscopy imaging at interfaces: evidence of interference effects," Institute Fresnel et al, XP-002597885, vol. 15, No. 16/Optics Express, published Aug. 2-6, 2007 (13 pages).

J. Lin et al., "Improved contrast radially polarized coherent anti-Stokes Raman scattering microscopy using annular aperture detection," Applied Science Letter 95. 133703 (2009), XP-12125904, published Oct. 1, 2009 (3 pages).

D. Gachet et al., "Revisiting the Young's Double Slit Experiment for Background-Free Nonlinear Raman Spectroscopy and Microscopy," Physical Review Letter PRL 104.213905 (2010) published May 26, 2010, corrected Jun. 1, 2010 (4 pages).

* cited by examiner

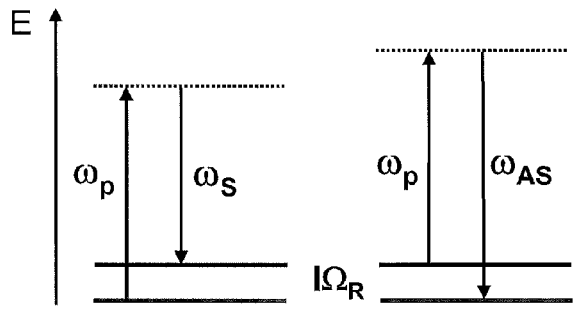
FIG.1A
Prior Art
FIG.1B
Prior Art
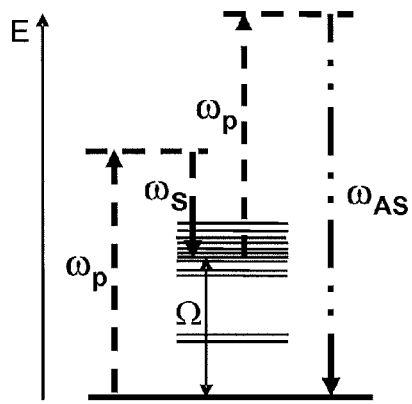
FIG.2A
Prior Art
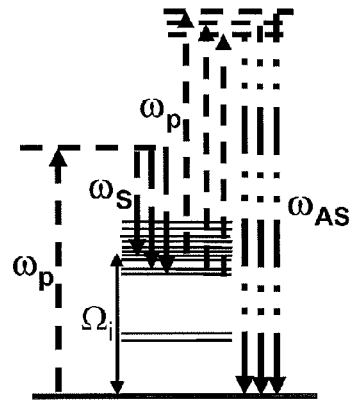
FIG.2B
Prior Art
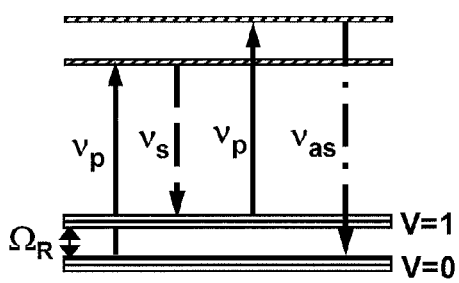
FIG.3A
Prior Art
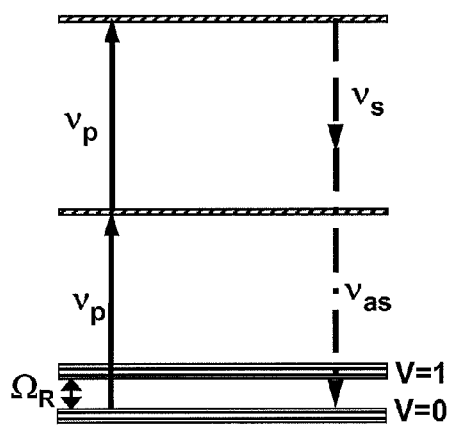
FIG.3B
Prior Art

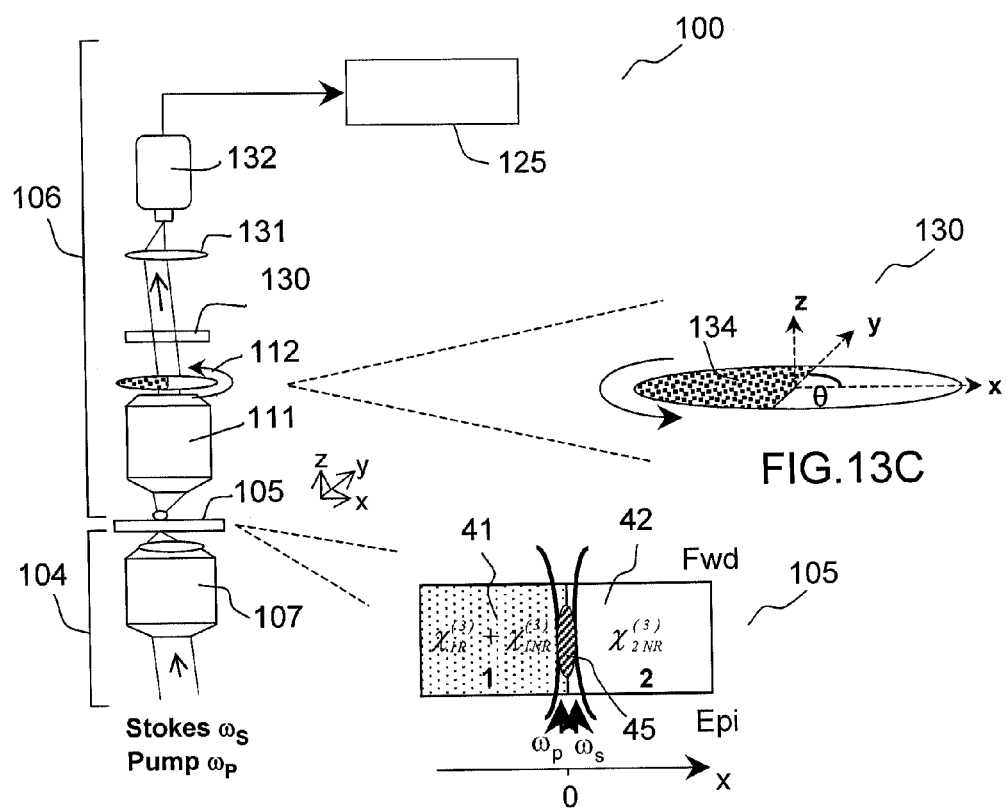

METHOD FOR DETECTING A RESONANT NONLINEAR OPTICAL SIGNAL AND DEVICE FOR IMPLEMENTING SAID METHOD

TECHNICAL FIELD OF THE INVENTION

The present invention relates to a method for detecting a resonant nonlinear optical signal and a device for implementing said method. It is particularly applicable to the detection of CARS scattering.

PRIOR ART

All chemical bonds have their own characteristic vibration frequency. Methods aimed at using the light/matter interaction to obtain information on these molecular vibrations are called vibrationally-sensitive optical techniques. The most well-known of these techniques is infrared (IR) spectroscopy, which observes the absorption lines specific to chemical bonds present in a sample. Discovered in 1928, Raman scattering (from the name of a physicist, Chandrasekhara Venkata Raman, who discovered the effect) allows visible light to be used to access the vibrational spectrum of molecules which interact with a light beam. In Raman scattering, a pump wave of angular frequency $\omega_P$ incident on a molecule is scattered inelastically into a wave called a Stokes wave, of angular frequency $\omega_S$ (FIG. 1A) and a wave called an anti-Stokes wave, of angular frequency $\omega_{AS}$ (FIG. 1B). The difference in frequency between the generated waves and the pump wave depends on the molecular Raman transition (of angular frequency $\Omega_R$) such that $\omega_p - \omega_s = \omega_{as} - \omega_p = \Omega_R$. In a photonic view of the process, the Stokes and anti-Stokes waves correspond to absorption from the fundamental or excited vibrational level respectively. The process generating the anti-Stokes wave, from the excited vibrational level (B), is much less probable than the process creating the Stokes wave, which is the only one observed in practice in spontaneous Raman spectroscopy. Detailed study of the spectral distribution of Stokes waves yields information about the densities of chemical bonds present in the sample. This spontaneous process of inelastic scattering is very inefficient compared with fluorescence (Raman cross-sections are of the order of $10^{-30}$ cm²/molecule, compared with the absorption cross-section of 1 photon of a fluorophore, which reaches $10^{-16}$ cm²/molecule).

Stimulated CARS (Coherent Anti-Stokes Raman Scattering) Raman spectroscopy is a four-wave mixing process that allows the vibrational bonds present in a sample to be addressed. This process is described, for example, in R. W. Boyd, *Nonlinear Optics* (Academic Press, Boston, 1992). It involves sending two laser pulses of angular frequencies $\omega_p$ and $\omega_s$ (or of frequencies $v_p$ and $v_s$), the angular frequency difference of which is equal to the angular frequency $\Omega$ at the vibrational level under investigation. In this resonance configuration $\omega_p - \omega_s = \Omega$, the vibrational level of angular frequency $\Omega$ is populated in a stimulated manner and will be able to scatter inelastically the beam of angular frequency $\omega_p$ into a beam of angular frequency $\omega_{as} = 2\omega_p - \omega_s$ (FIG. 2A). The presence of this new radiation $\omega_{as}$ (hereinafter referred to as a "CARS scattered signal") is the signature of the presence of the bond vibrating at the angular frequency $\Omega$ in the sample. A first implementation of CARS consists in directing at the sample two pulses which are spectrally picosecond narrow, the angular frequency difference of which addresses only one specific vibrational bond. For optimum identification, all the vibrational bonds present in the sample are tested. This is done by operating in a mode called "Multiplex CARS" (see, for example, M. Muller and J. Schins, "Imaging the thermodynamic state of lipidic membranes with multiplex CARS spectroscopy", Physical Chemistry B 106, 3715-3723 (2002)) where a spectrally narrow pulse $\omega_p$ and a spectrally wide pulse $\omega_s$ are directed at the sample (FIG. 2B). Thus all the vibrational levels $\Omega_i$ present in the sample can be addressed, and a spectrum of the generated signal $\omega_{as}$ can be obtained. From a technical point of view, the narrow spectrum originates, for example, from a picosecond laser and the wide spectrum, for example, from a femtosecond laser, or a photonic crystal fibre generating a supercontinuum (SC).

In FIG. 3A the process of resonant CARS scattering is described, which is used to access the signature of the molecular to be identified. However, a non-resonant CARS contribution exists, represented in FIG. 3B, which arises from an electronic contribution of the sample. This non-resonant contribution may be important when CARS spectroscopy is performed on a sample comprising a wide diversity of chemical bonds.

The patent application U.S. Pat. No. 6,809,814 in the name of Xie et al. describes detection of a CARS signal in a microscopic sample, based on backward (epi)-detection of the CARS signal, allowing the non-resonant noise of objects of size comparable to the wavelengths of sources of excitation to be eliminated. In particular, this detection mode enables visualisation of sub-wavelength size objects (organelles, for example) and suppression of the non-resonant background noise of the solvent generally surrounding biological samples. However, this detection has the drawback of not suppressing the intrinsic non-resonant background noise of these sub-wavelength objects.

Another technique for detecting the CARS signal allowing the non-resonant contribution to be eliminated is described in the patent application WO 2005/124322 in the name of Potma et al. The non-resonant CARS background noise is suppressed using a local oscillator and by undertaking a heterodyne detection. In practice, it involves generating the CARS signal in an accessory sample (in a solvent or an optical fibre, for example) and recombining it with the CARS signal generated by the sample of interest in the microscope while controlling its phase. This phase control requires an interferometric setup which is difficult to stabilise. In practice, this method is still at the laboratory demonstration stage.

In the patent application WO2008135257 in the name of Rimke et al., the heterodyne detection scheme disclosed in application WO 2005/124322 cited above is applied and the laser source used comprises a picosecond laser emitting at 1064 nm and duplicated at 532 nm. The 532 nm beam then pumps an optical parametric oscillator (OPO). The OPO generates two "signal" wavelengths $\lambda_{signal}$ and "idler" wavelengths $\lambda_{idler}$ tuneable according to $1/\lambda_{signal}(\text{nm}) + \lambda_{idler}(\text{nm}) = 1/532(\text{nm})$. The 1064 nm and idler beams therefore play the roles of pump and Stokes beams respectively. The signal beam is at the same wavelength as the anti-Stokes beam generated in the sample. It is recombined with the anti-Stokes beam and the signal resulting from this interference is detected according to the heterodyne interferometry process described in application WO 2005/124322. This very effective technique necessitates the use of an OPO able to generate the two signal and idler wavelengths.

Another technique for detecting the CARS signal allowing the non-resonant contribution to be eliminated is described in patent application U.S. Pat. No. 7,352,458 in the name of Xie et al. The non-resonant CARS background noise is suppressed by rapidly modulating (at frequency $v$) the anti-Stokes wavelength being observed. In practice, one of the two beams (pump or Stokes) is provided by a laser source delivering two wavelengths and the other beam is generated by a laser source at a single wavelength. The rapid modulation between the two wavelengths delivered by the first source allows the resonant and non-resonant excitation of the CARS signal to be modulated at the same frequency. The non-resonant noise of the CARS signal is thus suppressed by demodulating the CARS signal at frequency ν. In practice, this method necessitates a source emitting two wavelengths and a good contrast between the resonant and non-resonant signals between which the modulation operates.

Another technique for detecting the CARS signal allowing the non-resonant contribution to be eliminated is described in patent application U.S. Pat. No. 6,789,507 in the name of Xie and Cheng. It uses the various polarisation properties of resonant and non-resonant signals. It is known in spontaneous Raman spectroscopy that a vibrational resonance depolarises the excitation beam. In practice, the scattered beam is depolarised in relation to the excitation beam. This depolarisation effect is quantified by a "depolarisation coefficient" specific to each vibrational resonance. Applied to CARS scattering, the effect is used as follows: an angle is introduced between the linear polarisations of the pump and Stokes excitation beams. The resonant and non-resonant CARS signals are then generated according to different polarisations. A polariser is then introduced downstream of the sample to turn off the non-resonant signal and allow the fraction of the resonant signal not turned off to pass. This method is simple to implement but drastically reduces the resonant signal level detected. The closer the "depolarisation coefficient" of the probed Raman resonance is to $1/3$, the greater this reduction is.

The present invention proposes an original method for detecting a resonant nonlinear optical signal that is simple to implement, compatible with rapid imagery, and in particular allowing non-resonant CARS noise to be eliminated in microscopy or spectroscopy imaging applications. This method is based on analysis of the direction of scatter of the CARS signal at the axial interface of a resonant and non-resonant medium, and more precisely, on analysis of the angular deviation of the signal.

SUMMARY OF THE INVENTION

According to a first aspect, the invention relates to a device for detecting a resonant nonlinear optical signal induced in a sample of the type comprising a resonant medium and a non-resonant medium forming an interface. The device according to the first aspect comprises an emission source of at least one first excitation light beam, called a pump beam, at a first given angular frequency $\omega p$ for the excitation of the resonant medium of a sample of the given type, an optical detection module for detecting a nonlinear optical signal resulting from interaction of said incident pump beam with an axial interface between the resonant and non-resonant media of the sample, in at least two symmetrical directions about the optical axis of said pump beam incident upon the sample, and a processing unit for processing signals thus detected allowing the difference in the detected signals to be obtained, the resulting difference signal being characteristic of a vibrational or electronic resonance of the resonant medium of the sample. The device thus described allows the angular deviation of the nonlinear optical signal resulting from interaction of the beam or beams with the sample to be analysed, allowing a characteristic signal of a vibrational or electronic resonance of the resonant medium to be obtained at an axial interface of the resonant and non-resonant media.

According to a variant embodiment, the emission source allows the emission of a pump beam of angular frequency $\omega p$ and a Stokes beam of angular frequency $\omega s$, the nonlinear optical signal resulting from the interaction of said pump and Stokes beams is a signal called a CARS scattered signal, of angular frequency $\omega as = 2\omega p - \omega s$ and the signal resulting from the analysis of the direction of emission of the scattered CARS signal is a signal characteristic of a Raman emission of the resonant medium According to an embodiment, the optical detection module comprises at least one shadow mask and at least one detector, allowing detection of the nonlinear optical signal integrated into the two complementary half-spaces, symmetrical about the optical axis, the difference being effected on the integrated signals in the two half-spaces.

According to another variant embodiment, the optical detection module comprises an image recording system allowing the nonlinear optical signal collected in the directions symmetrical about the optical axis to be detected, point by point, the difference being effected for each signal couple thus detected.

According to another embodiment, the optical detection module for detecting said nonlinear optical signal comprises a mask rotating about the optical axis at a given frequency (ν), the mask partially occulting said signal, and a detector enabling the optical signal integrated in the part of the space not occulted by the mask to be detected, to deliver a modulated signal at said rotation frequency of the mask and having a maximum value and minimum value, and the one processing unit allows the processing of the modulated signal in order to obtain the amplitude of the angular frequency component of the signal at said frequency of rotation of the mask, the amplitude being proportional to the difference between said maximum and minimum values and being characteristic of a vibrational or electronic resonance of the resonant medium.

According to a variant embodiment, the device also comprises an angular scan device for scanning the excitation beam or beams, allowing the excitation beam or beams to intercept the sample at different positions of the interface between the resonant and non-resonant medium.

According to a variant embodiment, the emission source emits at least one variable wavelength excitation beam, allowing a spectrum of vibrational or electronic resonances of the resonant medium to be obtained.

According to a second aspect, the invention relates to a method for detecting a resonant nonlinear optical signal induced in a sample, the sample comprising a resonant medium and a non-resonant medium forming an interface, the method comprising: the emission of at least one first light beam for the excitation of the resonant medium, called a pump beam, at a first given angular frequency $\omega p$, said pump beam being incident on the sample along an optical axis, and intercepting said interface between the resonant medium and the non-resonant medium, the detection of the nonlinear optical signal resulting from interaction of the excitation beam or beams with an axial interface between the resonant and non-resonant media of the sample, in at least two directions symmetrical about the optical axis, and the processing of the signals thus detected allowing the difference between said signals to be obtained, the resulting difference signal being characteristic of vibrational or electronic resonance of the resonant medium of the sample.

According to a variant embodiment, the method comprises the emission of a pump beam of angular frequency $\omega p$ and of a Stokes beam of angular frequency $\omega s$, the nonlinear optical signal resulting from the interaction of said pump and Stokes beams being a signal called a CARS scattered signal, of angular frequency $\omega as = 2\omega p - \omega s$, and the signal resulting from analysis of the direction of emission of the CARS scattered signal being a signal characteristic of a Raman emission of the resonant medium.

According to a variant embodiment, the detection of the nonlinear optical signal is performed by integration of the signal into two complementary half-spaces, symmetrical about the optical axis, and the processing comprises calculating the difference between the signals integrated into the two half-spaces.

According to another embodiment, the detection of the nonlinear optical signal is a point-by-point detection of the nonlinear optical signal in directions symmetrical about the optical axis, and the processing comprises calculating the difference between the signals of each signal couple thus detected.

According to another embodiment, the detection of the nonlinear optical signal comprises partial occulting of said nonlinear optical signal by means of a mask rotating about the optical axis at a given frequency (ν) and the detection of the optical signal integrated into the part of the space not occulted by the mask to deliver a modulated signal at said rotation angular frequency of the mask having a maximum value and a minimum value and the processing comprises determining the amplitude of the angular frequency component at said rotation angular frequency of the mask of said modulated signal, the amplitude being proportional to the difference between said maximum and minimum values of the modulated signal and being characteristic of a vibrational or electronic resonance of the resonant medium.

According to a variant embodiment, the excitation beam or beams are subject to an angular scan to intercept the sample at various positions of the interface between the resonant and non-resonant medium.

According to a variant embodiment, at least one of the excitation beams has a variable emission wavelength, allowing a spectrum of vibrational or electronic resonances of the resonant medium to be obtained.

BRIEF DESCRIPTION OF THE DRAWINGS

Other advantages and characteristics of the invention will become apparent from reading the description, illustrated by the following Figs.:

FIGS. 1A and 1B (previously described), principle of Stokes and anti-Stokes emission in a Raman scattering process;

FIGS. 2A and 2B (previously described), principle of CARS emission in two different modes;

FIGS. 3A and 3B (previously described), illustrations of the resonant and non-resonant CARS process;

FIGS. 13A and 13C, diagram illustrating a device for implementing detection of the CARS scattering, according to another example embodiment of the invention;

DETAILED DESCRIPTION

Figure 4:
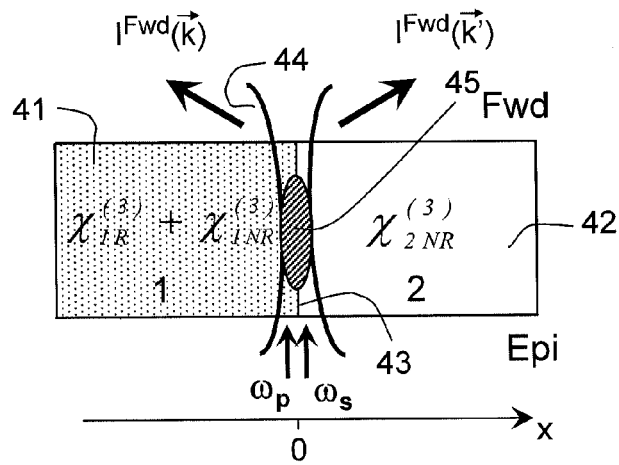
FIG. 4, diagram of the geometric conditions for implementing the CARS scattering at the interface of the resonant and non-resonant media.

FIG. 4 represents a sample comprising a resonant medium 41, for example a medium containing the medium to be analysed, in other words the medium of biological interest, and a non-resonant medium 42, typically a medium containing the solvent. The 3rd order nonlinear susceptibility is defined in the resonant medium 41 by a resonant term $\chi^{(3)}{}_{1R}$ and a non-resonant term $\chi^{(3)}{}_{1NR}$. In the non-resonant medium 42, it is defined by the non-resonant term $\chi^{(3)}{}_{2NR}$. According to one aspect of the detection method according to the invention, consists of analysing spatially the signal scattered by CARS process, reference numeral 44 in FIG. 4, resulting from the interaction of a pump excitation beam of angular frequency $\omega_p$ and probe excitation beam of angular frequency $\omega_s$, which are collinear, are incident on the sample in a focal volume 45, with an axial interface of the sample, in other words presenting a non-zero component along the axis of the incident pump and Stokes beams. More precisely, as is explained in detail in what follows, the method consists of analysing the nonlinear optical intensity of the beam in the space of wave vectors $\vec{k}$, in other words in the space of emission directions of the signal emitted by CARS, on both sides of the interface, this intensity being noted in FIG. 4 respectively $I^{Fwd}(\vec{k})$ and $I^{Fwd}(\vec{k}')$ on both sides of the interface. In the following description, the abbreviation "Fwd" represents the CARS forward scattered signal, as opposed to the signal known as "Epi", scattered in a backward direction.

Indeed, the Applicant has demonstrated experimentally and theoretically that at an axial interface, the signal emitted by the CARS process is subjected to an angular deviation at the resonance.

FIGS. 5A to 5E represent, by a series of diagrams, the deviation of the CARS scattered signal as a function of the relative position of the pump and Stokes beams incident with the interface. FIGS. 5A to 5E represent, the active CARS volume 45 (focal point of the pump and Stokes beams) which is displaced through a CARS object 50 (each label corresponds to a different position of the active volume in the object). The CARS object is considered as resonant when the medium surrounding the object is considered as non-resonant (in the rest of the description it will be called "the solvent"). It appears that, at the interfaces between the CARS object and the solvent, the CARS scattered signal is affected by a deviation (or tilt). The Applicant has demonstrated, as will be explained in the following, that this deviation arises from a purely interferential process between the CARS object and the solvent and is in no way due to refractive effects. In the two illustrations 1 (FIGS. 5A and 5E), the CARS volume is focused in the solvent and the CARS scattered signal is emitted in the normal direction (parallel to the axis of incidence of the pump and Stokes beams, symbolised by the arrow 51); on label 2 (FIG. 5B), the CARS volume is focused on the interface between the CARS object and the solvent, the CARS scattered signal is then emitted at a positive angle α (relative to the axis of incidence of the pump and Stokes beams), thus deviating the beam in a direction defined by ($k_x>0$) in the space of wave vectors $\vec{k}$. In illustration 3 (FIG. 5C), the CARS volume is centred in the CARS object, the CARS signal is then intense and is directed in the normal direction (parallel to the axis of incidence of the pump and Stokes beams). A similar situation is then found in the following illustrations (label 4, FIG. 5D and label 1, FIG. 5E); however, it is important to note that in illustration 4, α is negative and corresponds to a deviation in a direction defined by ($k_x<0$). The Applicant has demonstrated both theoretically and experimentally that the change in angle α as a function of the normalised parameter $\zeta=\omega_p-\omega_s-\Omega_R)/\Gamma$ (where Γ is the spectral width of the vibrational line studied), follows the phase of the tensor $\chi^{(3)}_1=\chi^{(3)}_{1R}+\chi^{(3)}_{1NR}$ describing medium 1. The Applicant has also demonstrated that it is possible, by analysing the CARS signal in symmetrical scattering directions about the optical axis of the incident beams, for example by taking the difference between the energies of CARS signals emitted in the complementary half-spaces defined by ($k_x>0$) and ($k_x<0$), to determine the pure Raman spectrum of medium 1.

Figure 6:
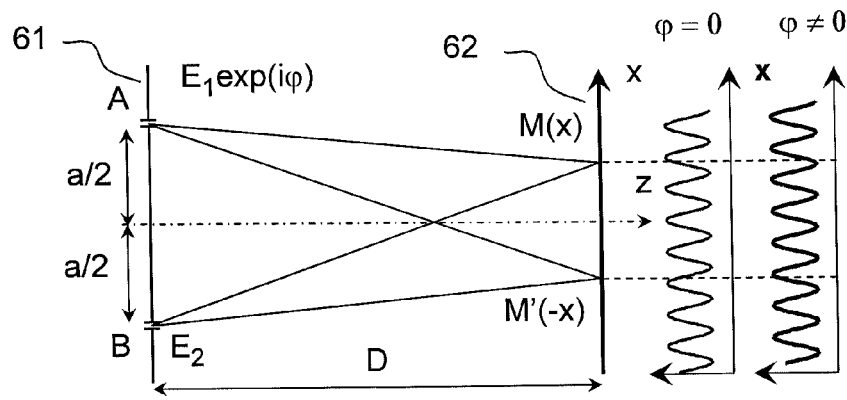
FIG. 6, diagram illustrating the experimental setup of Young's double-slit.

The applicant has demonstrated that this experimental finding could be explained by a simple model based on Young's double-slit theory. FIG. 6 shows the experimental setup of Young's double-slit; In Young's experiment, a monochromatic light source S (not shown in FIG. 6) illuminates a plate 61 perforated by two slits (labelled A and B). These behave as secondary light sources of amplitude E1 and E2. Alternating light and dark fringes are then observed, on a screen 62 placed at a distance D from plate 61, resulting from the interference of waves coming from A and B. The light intensity measured at a point M(x) of the screen 62 is written:

$$I(x) = |E_1|^2 + |E_2|^2 + 2|E_1||E_2|\cos\left(\frac{2\pi x}{\lambda D}\right)$$

If it is assumed that one of the secondary sources has a phase shift φ relative to the other, the intensity I(x) measured at M(x) is written:

$$I(x) = |E_1|^2 + |E_2|^2 + 2|E_1||E_2|\cos\left(\frac{2\pi x}{\lambda D} + \varphi\right)$$

The result of this is that the difference in intensity ΔI(x)=I(x)−I(−x) obtained by the intensity difference measured at two points M(x) and M'(−x) symmetrical about the axis of symmetry of the slits is written:

$$\Delta I(x) = 4|E_1||E_2|\sin\left(\frac{2\pi x}{\lambda D}\right)\sin(\varphi)$$

The Applicant has demonstrated that, by analogy, an expression of the difference $\Delta I(\vec{k})$ of intensities $I^{Fwd}(\vec{k})$ and $I^{Fwd}(\vec{k}')$ measured along two directions $\vec{k}$ and $\vec{k}'$ symmetrical about the axis of incidence of the pump and Stokes beams (FIG. 4) could be derived from the Young's double-slit theory:

$$\Delta I(\vec{k}) = I^{Fwd}(\vec{k}') - I^{Fwd}(\vec{k}) \propto 4|\chi_1^{(3)}||\chi_2^{(3)}|\sin(\phi)$$

Here, the phase shift φ originates from the signature of a molecular vibration of the resonant medium. It results from this expression that the difference $\Delta I(\vec{k})$ is proportional to the imaginary part of the 3rd order nonlinear susceptibility of the resonant medium, in other words the pure Raman spectrum of medium 1.

Figure 7:
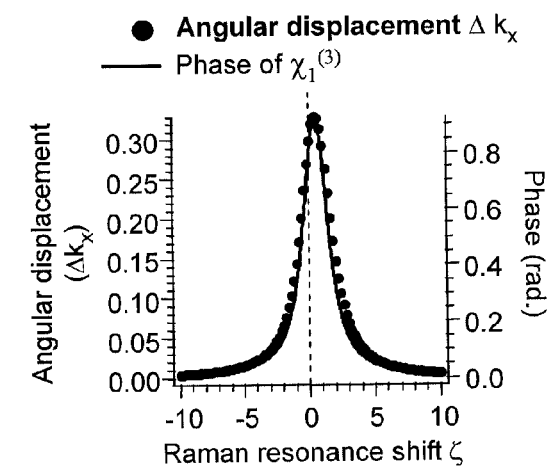
FIG. 7, curve obtained by numerical simulation, illustrating the deviation of the scattered CARS signal as a function of the parameter $\zeta=(\omega p-\omega s-\Omega R)/\Gamma$ (normalised shift to Raman resonance)
Figure 5:
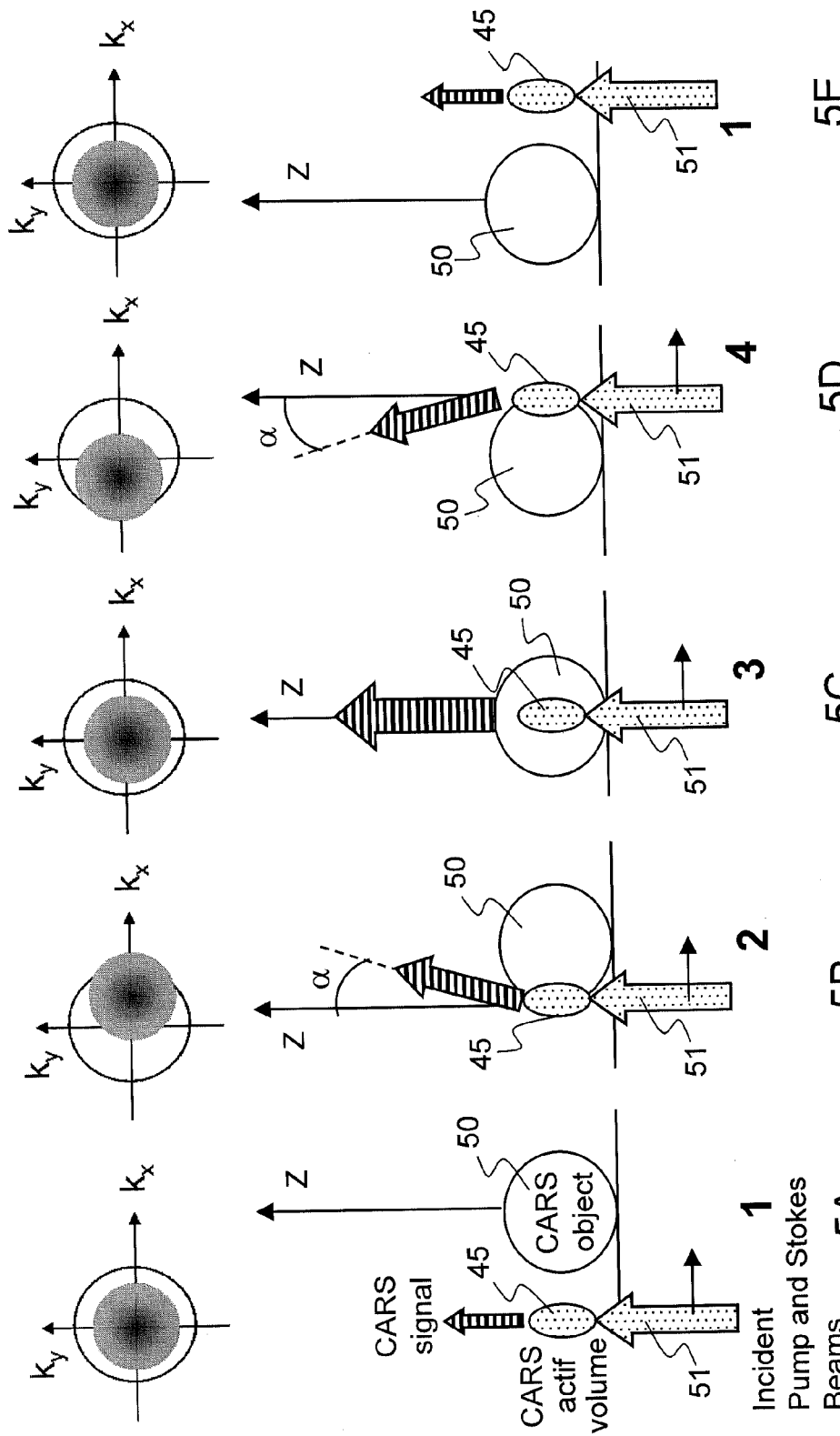
FIG. 5A to 5E, illustration of the deviation of the CARS scattered signal as a function of the relative position of the focal point of the excitation beams with the interface between resonant and non-resonant media.

FIG. 7 shows the results of a rigorous numerical calculation considering the vectorial nature of the pump and Stokes beams focused on an axial interface between a resonant medium 1 and a non-resonant medium 2 (FIG. 4). The analysis consists in studying in the space of wave vectors $\vec{k}$ the angular displacement of the CARS scattered signal emitted as a function of the normalised Raman shift $\zeta=(\omega_p-\omega_s-\Omega_R)/\Gamma$. Off-resonance (ζ=−10), the beam is centred, while on-resonance (ζ=0), an angular displacement clearly appears.

Figure 8A:
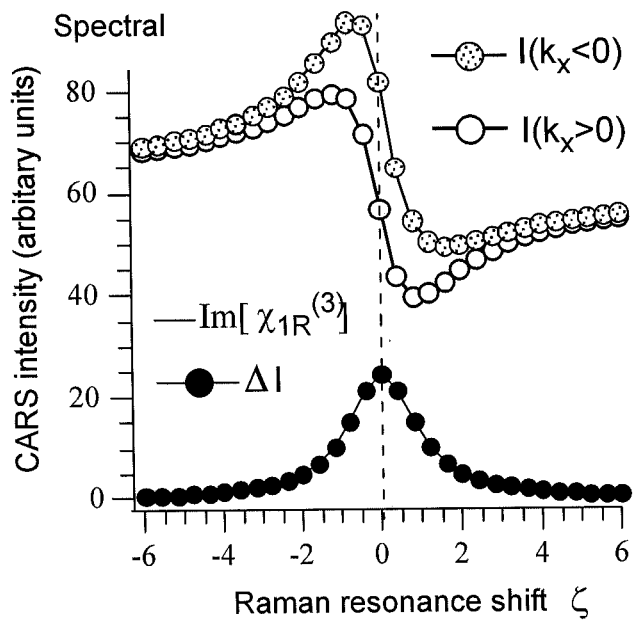
FIGS. 8A and 8B, curves obtained by numerical simulation, showing the light intensities calculated respectively in the space of ($k_x>0$) and ($k_x<0$) and the difference in intensities, as a function of the parameter $\zeta$ (FIG. 8A) and the x position of the focal point of the excitation beams relative to the interface (FIG. 8B)

FIG. 8A shows the CARS spectra integrated on the half-spaces ($k_x>0$) and ($k_x<0$) when the pump and Stokes beams are focused on the interface (x=0), as well as their difference ΔI. This difference exactly follows the Raman spectrum given by $Im[\chi^{(3)}_{1R}]$. This demonstrates the relevance of this approach for a CARS spectroscopy without non-resonant noise. Thus it is, for example, possible, by varying the frequency of the Stokes beam, to determine the Raman spectrum of the resonant medium.

Figure 8B:
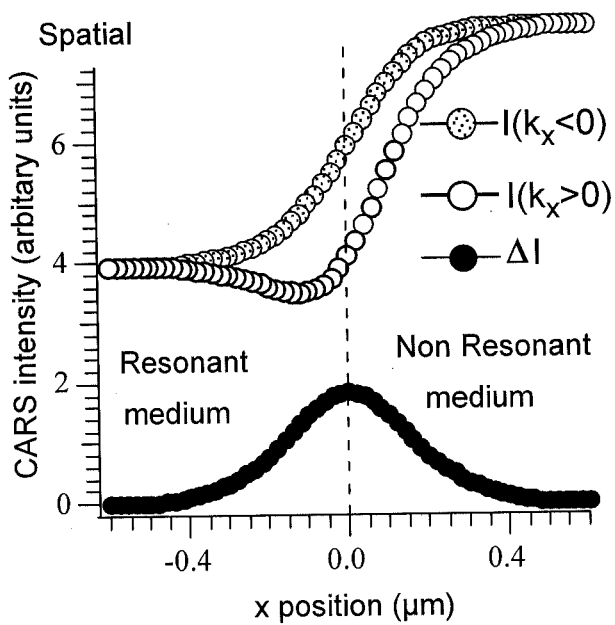

FIG. 8B represents the CARS signals integrated on half-spaces ($k_x>0$) and ($k_x<0$) as a function of the focal point of the pump and Stokes beams relative to the interface. Their difference is non-zero uniquely in the vicinity of the interface (x=0). A non-resonant CARS image without background noise can thus be obtained in the vicinity of the interface.

This new approach which finds the difference between CARS signals in the k space, is referred to in what follows as Dk-CARS (Differential imaging in K-space).

Figures 9A, 9B, 9C:
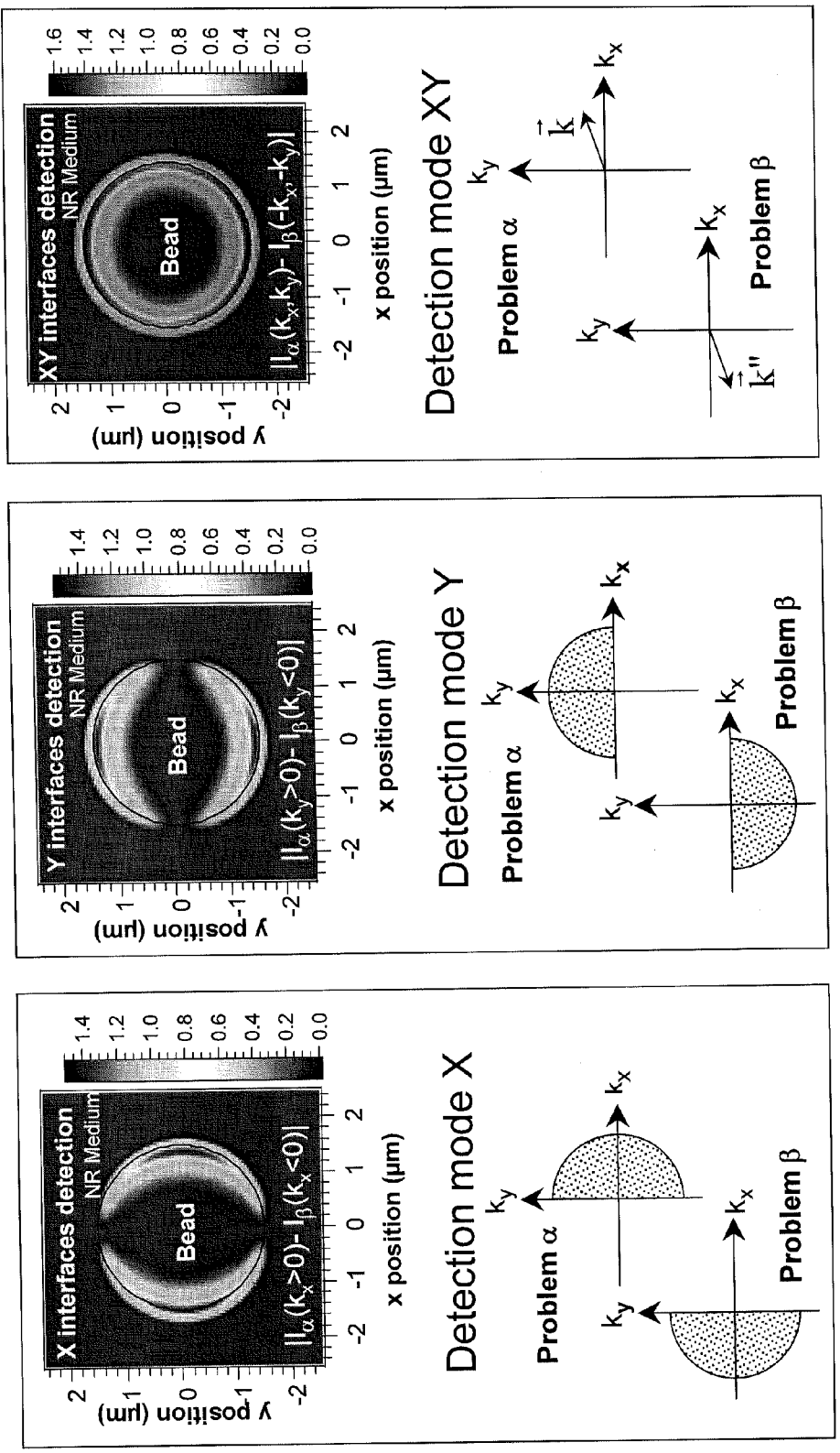
FIGS. 9A to 9C, diagrams illustrating 3 possible modalities for implementation of the CARS detection.
Figure 10:
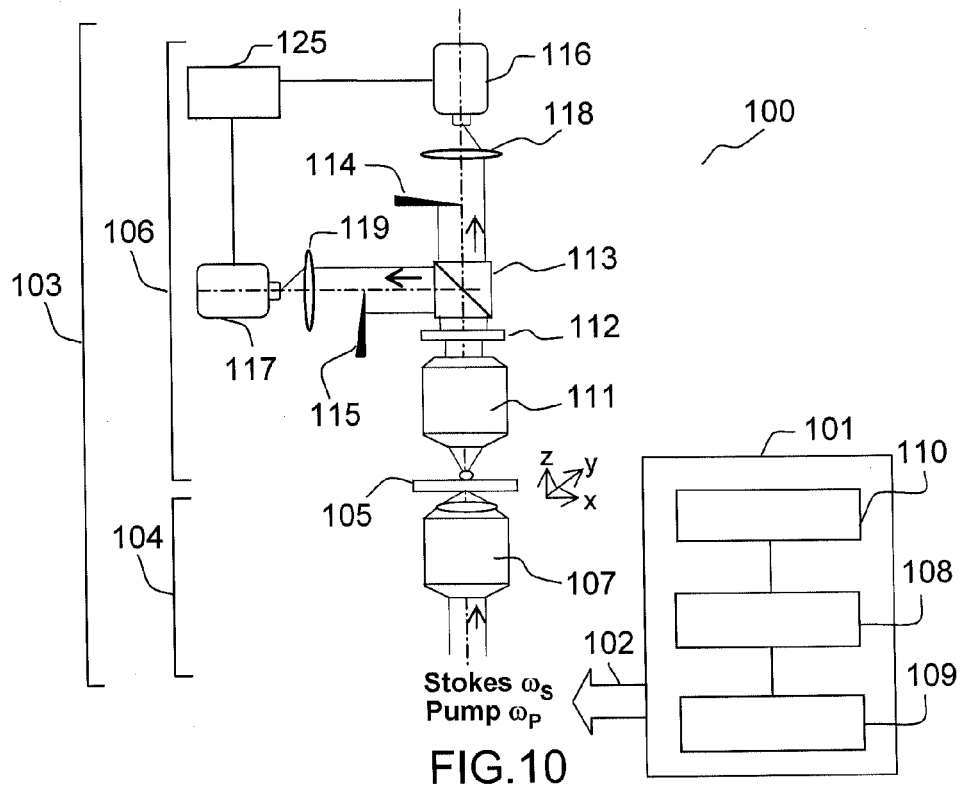
FIG. 10, diagram illustrating a device for implementing detection of the CARS scattering, according to an example embodiment of the invention.

FIGS. 9A and 9C show 3 possible detection modalities for Dk-CARS microscopy. For each detection modality, a numerical simulation represents the image obtained for a bead of 3-μm diameter in an aqueous solvent (pump wavelength 730 nm, Stokes wavelength 787 nm, numerical aperture in water of the excitation lens 1.2, numerical aperture in air of the collecting lens 0.5). The image is calculated in each case in a plane XY corresponding to the equatorial plane of the bead, perpendicular to the direction of incidence Z (see FIG. 5) of the excitation beams. FIG. 9A shows the X detection modality enabling detection at the interfaces perpendicular to the X axis. In the example of FIG. 9A, the difference of light intensity integrated in space ($k_x>0$) (case α, FIG. 9A) and in space ($k_x<0$) (case β, FIG. 9A). By changing the relative position of the focal point of the pump and Stokes beams, the image of FIG. 9A is obtained. FIG. 9B detection modality allowing detection at the interfaces perpendicular to the Y axis. In this example, for different positions, the difference in light intensities integrated in space ($k_y>0$) (case α, FIG. 9B) and in space ($k_y<0$) (case β, FIG. 9B) is calculated. FIG. 9C shows detection modality XYZ. The image is calculated by taking the two by two difference in light intensities $I_α(k_x, k_y)$ and $I_β(-k_x, -k_y)$ measured in two opposing directions $\vec{k}'(k_x, k_y, k_z)$ and $\vec{k}''(-k_x, -k_y, k_z)$, in cases α and β in FIG. 9C respectively, the directions being contained in the angular cone, the aperture angle of which is defined by the numerical aperture for collection of the CARS scattered signal (for example 0.5 in air. In this latter detection mode, all the interfaces are visible in an equatorial plane of the bead FIG. 10 shows a first example of experimental implementation of Dk-CARS, adapted, for example, to means of detection of FIG. 9A or 9B, for studying a sample comprising an interface between a resonant medium and a non-resonant medium. The detection device 100 according to FIG. 10 generally comprises a laser system 101 allowing a first excitation beam of angular frequency $ω_p$ (pump beam) and a second excitation beam of angular frequency $ω_s$ (Stokes beam) to be emitted, the two excitation beams symbolised by arrow 102 being collinear and incident according to a main direction Z in a optical detection module of the device overall referred to as 103. The optical detection module 103 overall comprises means 104 of making the excitation beams interact with a sample 105, positioned in a plane XY appreciably perpendicular to main direction Z, and means of analysing the direction of scatter of the CARS signal resulting from the interaction of the excitation beams with the sample 105, and more precisely, from the angular deviation of the CARS signal, comprising an optical detection module 106 and a processing unit 125.

The laser system 101 comprises, for example, in a so-called bi-colour application, two spectrally narrow, tunable laser sources 108, for example of Ti: Sapphire type, emitting at wavelengths between 690 and 1000 nm, pumped by a pump laser 109, Nd:YVO4 type emitting at 532 nm. The tuneable lasers emit, for example, picosecond (ps) pulses, typically of the order of 3 ps, to form a pump excitation beam of angular frequency $ω_p$ (of typical wavelength 730 nm) and Stokes excitation beam of angular frequency $ω_s$. A pulse picker 110 may be used to reduce the pulse repetition frequency of pump and probe excitation lasers without reducing the peak pulse power. Using a tuneable Stokes beam or pump beam enables, in particular, the anti-Stokes emission spectrum to be scanned for applications in spectroscopy aimed at determining the Raman spectrum of the resonant medium. Other tuneable laser sources may be used, for example, optical parametric oscillators (OPO), optical parametric amplifiers (OPA), picosecond Nd: glass oscillators, ytterbium or erbium-doped optical fibres, etc. The sources may also be nanosecond (ns) or femtosecond (fs) laser sources, depending on the spectral width of Raman lines to be observed. However, nanosecond pulses, although very good spectrally, have a lower peak power than ps pulses and a lower repetition frequency. Moreover, the thermal effects associated with ns pulses are more capable of damaging biological samples. Raw femtosecond pulses are generally too wide spectrally. In condensed phase (solid or liquid), line widths are around 10-20 cm$^{-1}$, corresponding to the use of picosecond pulses.

In the example of FIG. 10, the means 104 comprise, for example, a focusing lens 107 for focusing excitation beams aimed at focusing the pump and Stokes beams in a common focal volume for analysis of the sample. Using a focusing lens is particularly appropriate in microscopy applications. However, it is not essential for the emission of the CARS signal to work with focused beams, in particular where studying thin samples.

In the example of FIG. 10, the optical detection module 106 comprises a collecting lens 111 allowing collection of the nonlinear optical signal emitted, in this example the CARS signal, a filter 112 for cutting the excitation signals, an optical beamsplitter along two paths and on each path, a blade 114, 115, of the razor blade type, allowing two complementary half-spaces to be delimited. In the case of FIG. 10, the blades are arranged to delimit the two half-spaces ($k_x>0$) and ($k_x<0$) corresponding to mode of detection X (FIG. 9A). According to a variation, the blades could be arranged to delimit the two half-spaces ($k_y>0$) and ($k_y<0$) corresponding to the mode of detection Y (FIG. 9B). On each path, a detector 116, 117 arranged behind the blade allows measurement of the light intensity in each half-space. The detector is, for example, of the avalanche photodiode (APD), rapid photodiode (PIN) or photomultiplier (PMT) type. The detector may be preceded by a collecting optic 118, 119. A processing unit receives the signals detected by the detectors 116, 117 and determines the difference ΔI in light intensities measured on each of the paths, which the Applicant has shown to be proportional to the Raman spectrum of the resonant medium.

According to one example, the means 104 also comprise an excitation beam scanning device in plane XY of the sample. This scanning device can be useful at one and the same time in spectroscopy applications, for adjusting the focal point of the excitation beams over an axial interface of the resonant and non-resonant media forming the sample, that is, in imaging applications. It may act as a device allowing the displacement of the sample, or preferably, a device for angular scanning of the excitation beams (not shown in FIG. 10). When an angular scanning system for the excitation beams is provided, the excitation beams are incident along an axis (optical axis) which is no longer necessarily merged with the main direction Z. It will then be preferable to centre the components allowing the two half-spaces to be delimited in the exit pupil of the collecting lens, or an image of the exit pupil. Indeed, the positioning on the exit pupil allows the excitation beams to remain centred whatever their angle of incidence on the sample.

Figure 11:
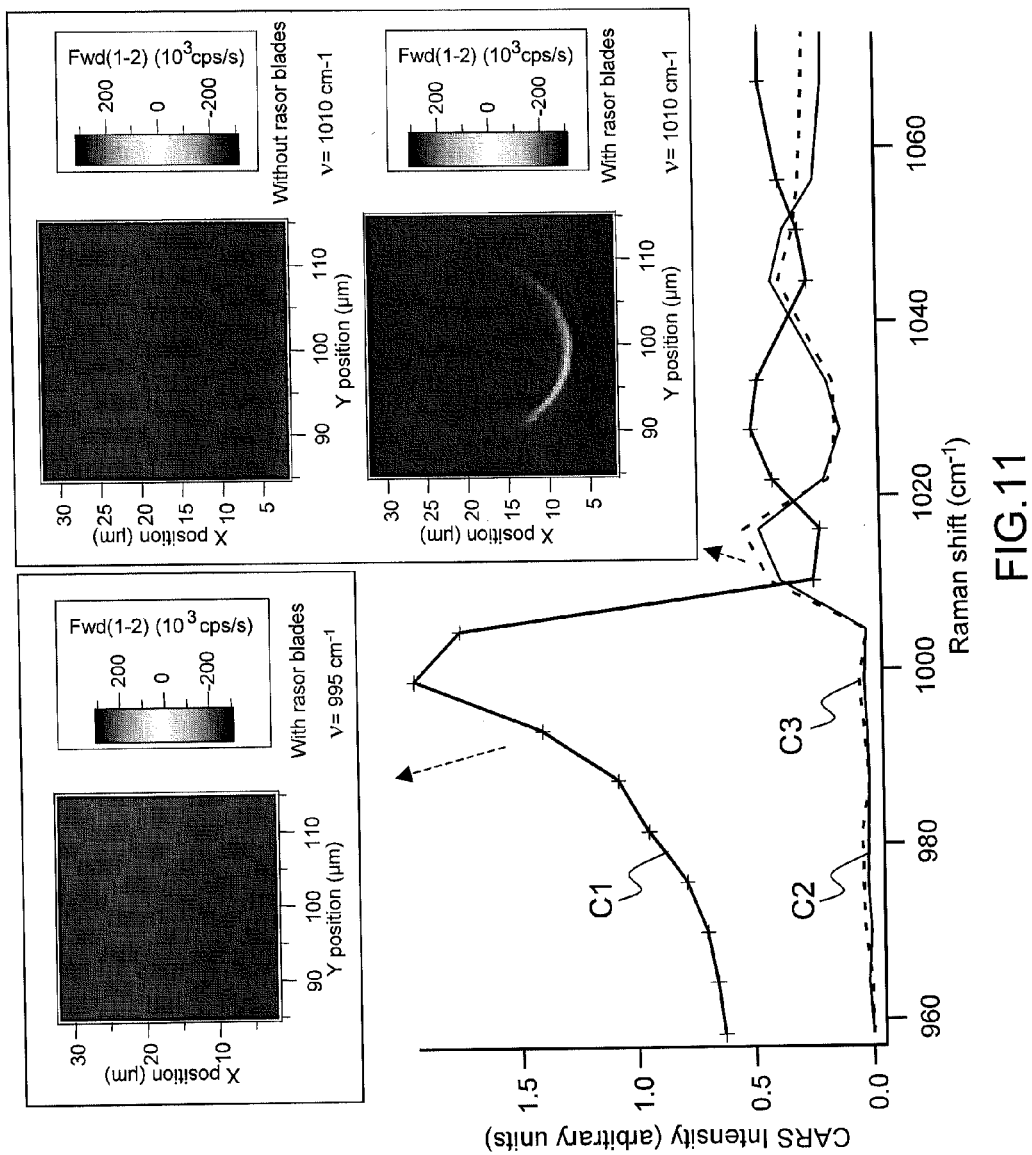
FIG. 11, experimental curve obtained with the diagram in FIG. 10, representing the intensity of the CARS scattering as a function of the Raman shift, for a polystyrene bead (20-μm diameter, immersed in an aqueous liquid with a refraction index of n=1.56)

FIG. 11 shows the experimental results obtained with the experimental setup of FIG. 10. The sample is made up of polystyrene beads (diameter 20 μm), the aromatic cycle of which has vibrational resonances at 1003 cm$^{-1}$ and 1034 cm$^{-1}$. These beads are submerged in an aqueous liquid of refractive index n=1.56 and are excited by a lens having a numerical aperture in water of 1.2. The wavelength of the pump beam is set at 730 nm and the wavelength of the Stokes beam is made to vary in such a way as to pass the Raman resonance mentioned above. Curve C1 represents the CARS intensity, in other words the light intensity integrated throughout the space. Curve C2 (solid line) represents the difference in intensities ΔI measured in the half-spaces ($k_x>0$) and ($k_x<0$) respectively.

Off-resonance at 995 cm$^{-1}$, the difference ΔI does not give any signal. On the other hand, at 1010 cm$^{-1}$ by using occulting blades as described in FIG. 10, the interfaces following the x direction illuminate, revealing the awaited result (see FIG. 8B). If the blades are removed, no signal appears because the detectors 116, 117 (FIG. 10) see the same signal. Spectrally, curves C2 and C3 represent the change in ΔI as a function of $ω_p-ω_s$ at two opposing interfaces between the bead and the liquid. The applicant has demonstrated that these curves follow the Raman spectrum, with minor experimental uncertainty errors.

FIG. 10 thus shows a particularly simple embodiment for implementing Dk-CARS detection. Numerous variants are possible.

According to one variant embodiment, the razor blades 115, 116 may be replaced by any type of shadow mask allowing two complementary half-spaces to be delimited. For example, these masks can be arranged directly on the optical beamsplitter 113.

According to another variant embodiment, the optical detection module 106 comprises only a single path, with a single detector, of the avalanche photodiode or photomultiplier type, by using an adaptive filter, for example an electrically controlled liquid crystal filter. In this case, the intensity integrated on one half-space is measured first, then the intensity is measured on the other half-space and a calculation is made of the difference between the intensities.

Figure 12:
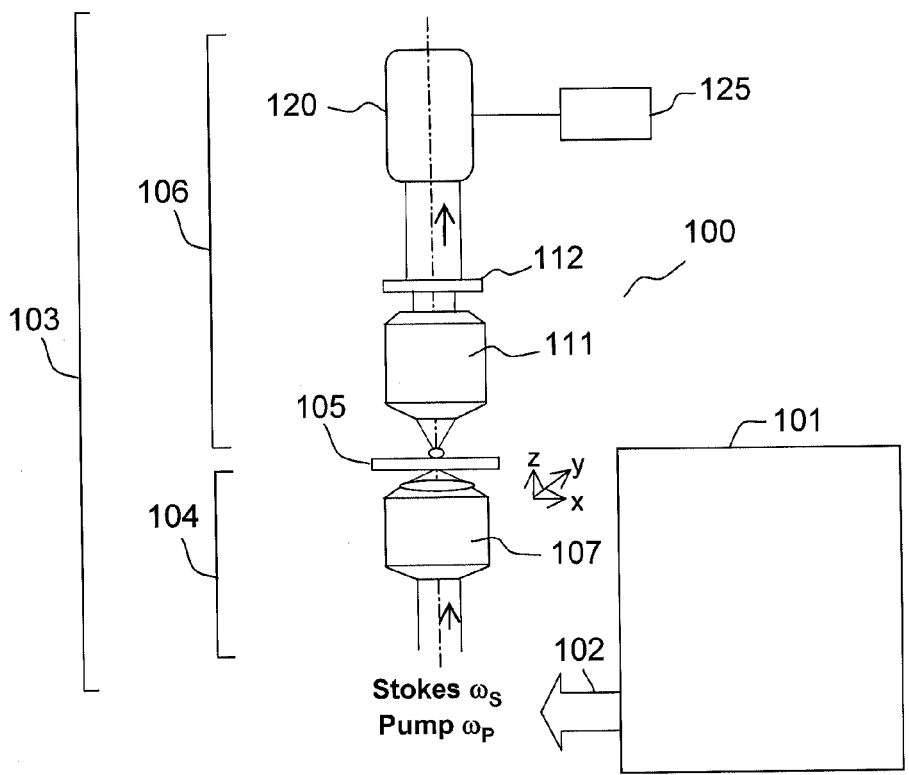
FIG. 12, diagram illustrating a device for implementing detection of the CARS scattering, according to another example embodiment of the invention.

FIG. 12 shows a variation of FIG. 10, in which the means of analysis of the scatter direction of the CARS signal comprises an optical detection module 106 with a single path, adapted to detection in XY mode (FIG. 9C). According to this variation, the shadow masks system is replaced by a single detector formed of an image recording system, for example a matrix camera of CCD or CMOS type, having a 4 quadrant photodiode. Using the camera allows point-by-point detection of the nonlinear optical signal emitted in a direction symmetrical relative to the direction of incidence of the excitation beams on the camera (when filter 112 has been removed), the difference being taken for each signal couple thus detected.

In practice, in a microscopy application, for example, in which the excitation beams are scanned on the sample, the direction of incidence of excitation beams varies and calibration can be performed, for example, by marking the position of the excitation beams on the detector, for the different scanning positions. The camera may also be calibrated "in solution". To do this, one could for example mark the position of the signal, for different angles of incidence of the excitation beams, when the excitation beams are focused in a homogenous CARS medium and there is therefore no deviation of the CARS scattered signal. The shift is then measured relative to this reference position.

In microscopy applications, when a scanning system for pump and Stokes excitation beams is used, it is preferable to position the camera in the exit pupil of the collecting lens, or an image of the exit pupil. This enables the excitation beams to remain centred whatever their angle of incidence on the sample. Otherwise, it is possible to calibrate the camera to take into account the position of the incident excitation beams for various scanning angles, this position serving as a reference for measuring the shift in the nonlinear optical signal.

FIGS. 13 to 16 illustrate another variant of the means of analysis of the direction of emission of the CARS signal. As in the preceding examples, a sample 105 (FIG. 13B) comprising a resonant medium and a non-resonant medium forming an interface is excited by a pump beam and a Stokes beam, which are collinear and incident on the sample according to a common focal volume 45. In the example illustrated in FIG. 13A, the optical detection module 106 comprises mask 130 rotating about the main direction Z at a given frequency (ν). This mask, for example, shaped as a half-disc 134 as shown in FIG. 13C, partially occults the scattered CARS signal in an XY plane perpendicular to the main direction Z. The signal thus occulted is detected by a detector 132, for example those of the type of the photomultiplier, photodiode PIN or avalanche photodiode type, preceded by a focusing lens 131.

Figures 14A, 14B:
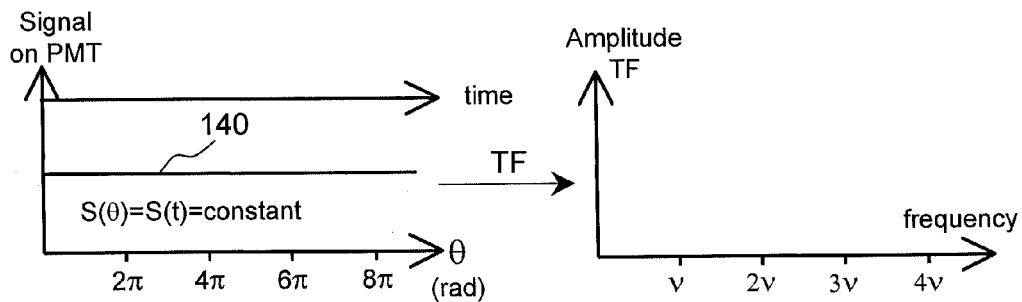
FIGS. 14A and 14B, diagrams illustrating the signal measured under the experimental conditions of FIG. 13A, off-resonance.
Figures 15A, 15B:
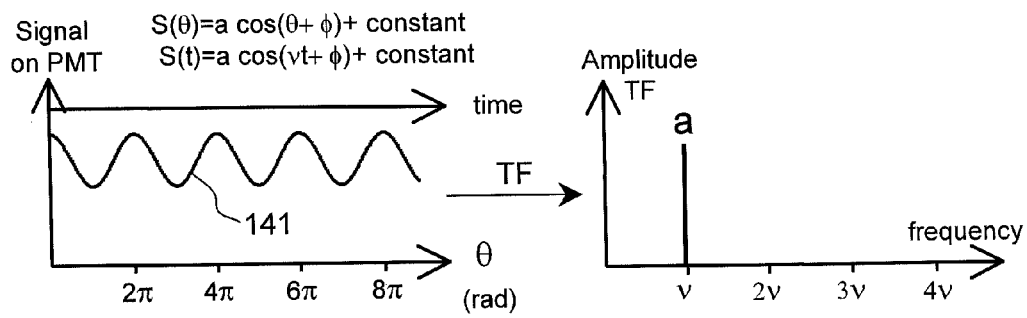
FIGS. 15A and 15B, diagrams illustrating the signal measured under the experimental conditions of FIG. 13A, on-resonance.

Off-resonance, the scattered CARS signal is centred and the signal detected by the detector 132 is constant as a function of the angular position θ of the mask (θ being, for example, defined in relation to the x axis, as illustrated in FIG. 13C). As is apparent from FIG. 14A, the signal detected S(θ) is constant. In the Fourier space, the harmonics of the signal at frequency ν are zero (FIG. 14B).

At resonance, the scattered CARS signal is deviated, it is no longer centred on the rotating mask and the signal detected by the detector 132 (curve 141, FIG. 15A) is thus modulated according to the equation:

$$S(\theta) = a \cos(\theta + \phi) + \text{constant}$$

Or $$S(t) = a \cos(\nu t + \phi) + \text{constant}$$

The processing unit 125 allows the signal to be demodulated at frequency ν, by calculating the Fourier transform or, preferably, by means of synchronous detection, in order to determine the amplitude (non-zero) of the Fourier transform at frequency ν. This amplitude is proportional to the difference between the maximum and minimum values of signal S(t). It is proportional to the imaginary part $\text{Im}[\chi^{(3)}{}_{1R}]$ of medium 1; it is thus characteristic of a vibrational resonance of the resonant medium and thus allows the Raman spectrum to be determined in a spectroscopy or microscopy application, to obtain contrasted images at axial interfaces.

Figure 16:
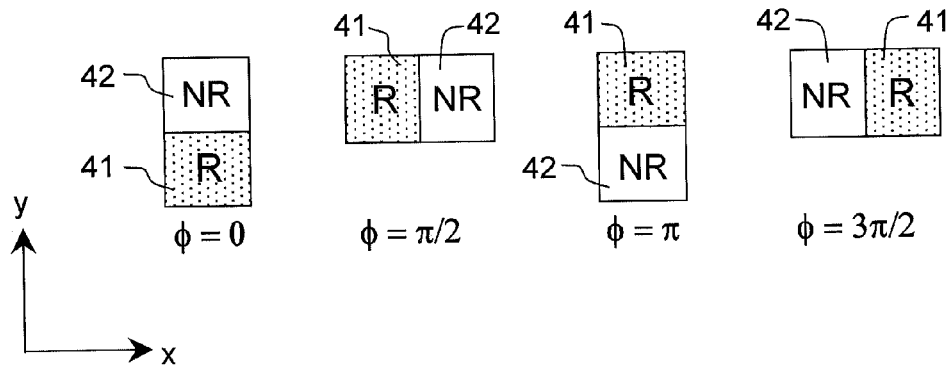
FIG. 16, a diagram showing the determination of the orientation of the interface and the relative position of the resonant and non-resonant media using the device according to FIG. 13A.

Moreover, as illustrated in FIG. 16, determining phase φ of the signal modulated at the first harmonic ν, obtained by Fourier transform, provides information about the orientation and relative position of resonant and non-resonant media.

Shapes other than a half-disc may be used for the rotating mask, such as a quarter of a disc or three quarters of a disc, for example. Furthermore, the rotating mask may be produced mechanically, as described, or by means of an electrically controllable filter, for example a liquid crystal filter.

FIG. 13A shows the application of the microscopy method, when a scanning system for pump and Stokes excitation beams is used. In this example, it is preferable to position the rotating disc in the exit pupil of the collecting lens, or an image of the exit pupil, so that the excitation beams remain centred whatever their angle of incidence on the sample.

For implementation of Dk-CARS, the scattering direction of the CARS signal is analysed in the distant field. Use of the collecting lens 111 (FIGS. 10, 12, 13A) facilitates experimental implementation. However, this collecting lens is not strictly necessary and the detection could be done directly downstream of the sample.

CARS detection has been described in a bi-colour application, using two spectrally narrow laser sources. In an application called multiplex, a spectrally wide emission source of the Stokes beam can be chosen, generated, for example, by a femtosecond pulse or by a supercontinuum generated by an optical fibre or another dispersive medium. The pump signal itself remains spectrally narrow. In this application, it will be possible to acquire a Raman spectrum in a single pulse, for example, by using two slit spectrometers or a single spectrometer equipped with a CCD camera into which the two signals detected into the two half-spaces are injected. In this application, it is a matter of acquiring the spectrums in the half spaces ($k_x > 0$) and ($k_x < 0$) and taking their difference.

In an application called a tricolour application, three wavelengths of associated frequencies $\omega_1$, $\omega_2$ and $\omega_3$ are used to generate a CARS signal at angular frequency $\omega_1 - \omega_2 + \omega_3$. The CARS signal may be rendered non-resonant without noise by detecting the signals at the angular frequency $\omega_1-\omega_2+\omega_3$ in the half-spaces ($k_x$>0) and ($k_x$<0) and taking their difference.

Although the detection method has been described in the case of CARS scattering, it applies just as well to other nonlinear, 2nd or 3rd order processes, both for spectroscopy applications and for microscopy applications by detection at axial interfaces, thus enabling the interfaces between the resonant and non-resonant media to be revealed. In each case, an analysis of the direction of emission of the nonlinear optical signal resulting from the interaction of one or more excitation beams is performed with a sample presenting an interface between a resonant medium and a non-resonant medium. This analysis of the direction of emission allows either the interface between the resonant medium and the non-resonant medium to be revealed, or a spectrum of the resonant medium to be characterised.

According to one example, a process for generating the third resonant harmonic can be used wherein the resonance is an electronic resonance, by exciting a sample comprising an interface between a resonant medium and a non-resonant medium with a single pump excitation beam, of angular frequency $\omega_p$. For example a picosecond or femtosecond laser source of the oscillator types Ti: Sapphire, Nd: glass, or ytterbium or erbium-doped optical fibres.

According to another example, a four-wave mixing process can be used wherein the resonance is an electronic resonance, by exciting a sample comprising an interface between a resonant medium and a non-resonant medium with a single pump excitation beam, of angular frequency $\omega_p$. For example a picosecond or femtosecond laser source of the oscillator types Ti: Sapphire, Nd: glass, or ytterbium or erbium-doped optical fibres.

The two examples described above deal with electronic resonances. They are found in atoms, molecules, semi-conductor crystals, etc.

According to another embodiment, the second resonant harmonic can be excited with a single pump beam, or the sum of the frequency can be made with a pump beam and probe beam (nonlinear effect of the 2nd order).

Although described using a certain number of detailed example embodiments, the detection device and method according to the invention comprise different variants, modifications and developments which will be obvious to the person skilled in the art, it being understood that these different variants, modifications and developments fall within the scope of the invention, as defined by the claims below.

The invention claimed is:

1. Device (100) for detecting a resonant nonlinear optical signal induced in a sample (105) of a type comprising a resonant medium (41) and a non-resonant medium (42) forming an interface (43), the device comprising:
   an emission source (801) of at least one first excitation light beam, called a pump beam, at a first given angular frequency $\omega_p$ for the excitation of a resonant medium of a sample of the given type,
   an optical detection module (106) for detecting a nonlinear optical signal resulting from the interaction of said pump beam with an axial interface between the resonant and non-resonant media of the sample, in at least two symmetrical directions ($\vec{k}$, $\vec{k}'$) about the optical axis of said incident pump beam incident in the sample, and
   a processing unit (125) for processing the signals thus detected along the at least two symmetrical directions, allowing the difference in detected signals to be obtained, the resulting difference signal being characteristic of a vibrational or electronic resonance of the resonant medium.

2. Device according to claim 1, in which the emission source (801) allows the emission of at least a second excitation beam for excitation of the resonant medium, at at least a second angular frequency $\omega$s different from the first angular frequency $\omega$p, the excitation beams being collinear, said difference signal obtained being characteristic of a vibrational or electronic resonance of the resonant medium at an angular frequency equal to the linear combination of the excitation beam frequencies.

3. Device according to claim 2, in which the emission source allows the emission of a pump beam of angular frequency $\omega$p and a Stokes beam of angular frequency $\omega$s, allowing a nonlinear signal called CARS scattered signal to be generated in a sample of the given type, of angular frequency $\omega$as=2$\omega$p−$\omega$s, said obtained signal difference being characteristic of a Raman emission of the resonant medium.

4. Device according to any one of the previous claims, comprising a focusing lens (107) for focusing said excitation beam or beams in a common focal volume (45), to intercept an interface between the resonant medium and the non-resonant medium of a sample of the given type.

5. Device according to any one of the preceding claims, in which the optical detection module (106) comprises at least one shadow mask and at least one detector, enabling detection of the non-linear optical signal integrated into two complementary half-spaces, symmetrical about the optical axis, the difference being taken of the signals integrated into the two half-spaces.

6. Device according to claim 5, in which the optical detection module (106) comprises
   an optical splitting element (113) for separating the collected nonlinear optical signal in a first and second path, and
   on each path, a shadow mask (114, 115) for occulting the nonlinear optical signal and a detector (116, 117), the signals in each path being occulted respectively according to the two semi-spaces.

7. Device according to any of claim 5 or 6, in which the optical detection module comprises a collecting lens (111) for collecting said nonlinear optical signal.

8. Device according to claim 7, in which the shadow mask or masks are centred on the exit pupil or on an image of the exit pupil of the collecting lens.

9. Device according to any one of claims 1 to 4, in which the optical detection module (106) comprises an image recording system (120) allowing point-by-point detection of the nonlinear optical signal collected in directions symmetrical about the optical axis, the difference being taken of each signal couple thus detected.

10. Device according to claim 9, in which the optical detection module comprises a collecting lens for collecting said nonlinear optical signal.

11. Device according to claim 10, in which the image recording system is placed on the exit pupil or on an image of the exit pupil of the collecting lens.

12. Device according to any claims 1 to 4, in which:
   the optical detection module (106) of said nonlinear optical signal comprises a mask (130) in rotation about the optical axis at a given frequency (v), the mask partially occulting said signal, and a detector allowing detection of the optical signal integrated into the part of the space not occulted by the mask to deliver a signal modulated at said rotation frequency of the mask and having a maximum value and a minimum value, and the processing unit (125) allows the processing of said modulated signal in order to obtain the amplitude of the frequency component of the signal at said rotation frequency of the mask, the amplitude being proportional to the difference between said maximum and minimum values and being characteristic of a vibrational or electronic resonance of the resonant medium.

13. Device according to claim 12, in which the processing unit also allows the phase of the frequency component of the modulated detected signal to be obtained, the phase being characteristic of the relative position of the resonant and non-resonant media.

14. Device according to any one of claim 12 or 13, in which the mask comprises a half-disc (134) rotating about the optical axis.

15. Device according to any of claims 12 to 14, in which the optical detection module comprises a device for collecting said nonlinear optical signal.

16. Device according to claim 15, in which the mask is centred on the exit pupil of the collection device, or on a pupil image of said exit pupil.

17. Device according to any one of the preceding claims, also comprising a device for angular scanning of the excitation beam or beams, allowing the excitation beam or beams to intercept a sample of the given type at different positions of the interface between the resonant medium and the non-resonant medium.

18. Device according to any one of the preceding claims, in which the emission source emits at least one variable wavelength excitation beam, allowing a spectrum of vibrational or electronic resonances of the resonant medium of a sample of the given type to be obtained.

19. Method for detecting a resonant non-linear optical signal induced in a sample (105), the sample comprising a resonant medium (41) and a non-resonant medium (42) forming an interface (43), the method comprising:
  the emission of at least one first excitation light beam of the resonant medium, called a pump beam, at a first given angular frequency $\omega_p$, said pump beam being incident on the sample along an optical axis, and intercepting said interface between the resonant medium and the non-resonant medium,
  the detection of the nonlinear optical signal resulting from the interaction of said beam or beams with an axial interface between the resonant and non-resonant media of the sample, in at least two symmetrical directions ($\vec{k}$, $\vec{k}'$) about the optical axis, and
  the processing of the nonlinear optical signals thus detected along the at least two symmetrical directions, allowing the difference between said signals to be obtained, the resulting difference signal being characteristic of a vibrational or electronic resonance of the resonant medium of the sample.

20. Method according to claim 19, comprising emission of at least one second excitation beam of the resonant medium, at at least one second angular frequency ωs different from the first angular frequency ωp, the excitation beams being collinear, difference signal being characteristic of a vibrational or electronic resonance of the resonant medium at a frequency equal to the linear combination of the frequencies of the excitation beams.

21. Method according to claim 20, comprising the emission of a pump beam of angular frequency ωp and a Stokes beam of angular frequency ωs, the nonlinear optical signal resulting from the interaction of said pump and Stokes beams being a signal called a CARS scattered signal, of angular frequency ωas=2ωp−ωs and the difference signal being characteristic of a Raman emission of the resonant medium.

22. Method according to any one of claims 19 to 21, in which the said excitation beam or beams are focused into a common focal volume (45), allowing said interface to be intercepted between the resonant medium and non-resonant medium.

23. Method according to any one of claims 19 to 22, in which the detection of the nonlinear optical signal is achieved by integration of the signal into two complementary semi-spaces, symmetrical about the optical axis, and the processing comprises calculation of the difference between the signals integrated into the two semi-spaces.

24. Method according to any one of claims 19 to 22, in which the detection of the nonlinear optical signal is achieved by point-by-point detection of the nonlinear optical signal in directions symmetrical about the optical axis, and the processing comprises calculating the difference between the signals of each signal couple thus detected.

25. Method according to any of claims 19 to 22, in which:
  the detection of the nonlinear optical signal comprises the partial occulting of said nonlinear optical signal by means of a mask (130) rotating about the optical axis at a given frequency (ν), and detection of the optical signal integrated into the part of the space not occulted by the mask to deliver a modulated signal at said rotation frequency of the mask having a maximum and minimum value,
  the processing comprises determining the amplitude of the frequency component at said rotation frequency of the mask of said modulated signal, the amplitude being proportional to the difference between said maximum and minimum values of the modulated signal and being characteristic of a vibrational or electronic resonance of the resonant medium.

26. Method according to claim 25, also comprising determination of the phase of the frequency component of the modulated detected signal, the phase being characteristic of the relative position of the resonant and non-resonant media.

27. Method according to any one of claims 19 to 26, in which the excitation beam or beams are subject to angular scanning to intercept the sample at various positions of the interface between the resonant and non-resonant medium.

28. Method according to any one of claims 19 to 27, in which at least one of the excitation beams has a variable emission wavelength, allowing a spectrum of the vibrational or electronic resonances of the resonant medium to be obtained.

* * * * *